(12) United States Patent
Wendelken et al.

(10) Patent No.: US 11,596,346 B2
(45) Date of Patent: Mar. 7, 2023

(54) SIGNAL PROCESSING FOR DECODING INTENDED MOVEMENTS FROM ELECTROMYOGRAPHIC SIGNALS

(71) Applicant: University of Utah Research Foundation, Salt Lake City, UT (US)

(72) Inventors: Suzanne Wendelken, Salt Lake City, UT (US); Tyler Davis, Salt Lake City, UT (US); David Page, Salt Lake City, UT (US); David Kluger, Salt Lake City, UT (US); David Warren, Salt Lake City, UT (US); Gregory Clark, Salt Lake City, UT (US); Christopher Duncan, Salt Lake City, UT (US); Jacob Nieveen, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 323 days.

(21) Appl. No.: 16/322,855

(22) PCT Filed: Aug. 1, 2017

(86) PCT No.: PCT/US2017/044947
§ 371 (c)(1),
(2) Date: Feb. 1, 2019

(87) PCT Pub. No.: WO2018/026842
PCT Pub. Date: Feb. 8, 2018

(65) Prior Publication Data
US 2022/0022801 A1    Jan. 27, 2022

Related U.S. Application Data

(60) Provisional application No. 62/512,576, filed on May 30, 2017, provisional application No. 62/369,496, filed on Aug. 1, 2016.

(51) Int. Cl.
*A61B 5/389* (2021.01)
*G06K 9/62* (2022.01)
(Continued)

(52) U.S. Cl.
CPC ............... *A61B 5/389* (2021.01); *A61F 2/72* (2013.01); *G06K 9/6256* (2013.01); *G06N 7/00* (2013.01);
(Continued)

(58) Field of Classification Search
CPC ........... A61B 5/389; A61B 2562/0252; A61B 2562/046; A61B 2505/09; A61B 5/7275;
(Continued)

(56) References Cited

U.S. PATENT DOCUMENTS 6,865,409 B2    3/2005   Getsla et al.
7,623,928 B2    11/2009  DiLorenzo
(Continued)

FOREIGN PATENT DOCUMENTS

CN    102138860 A    8/2011
CN    103190905 A    7/2013

OTHER PUBLICATIONS

Yeom, H. J., et al. "An adaptive M-wave canceler for the EMG controlled functional electrical stimulator and its FPGA implementation." The 26th Annual International Conference of the IEEE Engineering in Medicine and Biology Society. vol. 2. IEEE, 2004. (Year: 2014).*
(Continued)

*Primary Examiner* — David J. McCrosky
*Assistant Examiner* — Nidhi N Patel
(74) *Attorney, Agent, or Firm* — Thorpe North and Western LLP

(57) ABSTRACT

A technology is described for determining an intended movement from neuromuscular signals. An example method
(Continued)

(800) includes receiving electromyography (EMG) data corresponding to single-ended channels of an electrode array (810), where EMG signals are detected by electrodes comprising the single-ended channels of the electrode array and the EMG signals are converted to the EMG data. Determining differential channel pairs for the single-ended channels of the electrode array (820) and extracting feature data from the EMG data of the differential channel pairs (830). Thereafter a feature data set is selected from the feature data of the differential channel pairs (840) and the feature data set is input to a decode model configured to correlate the feature data set to an intended movement (850). Decode output is received from the decode model indicating the intended movement (860) and the decode output is provided to a device (870).

22 Claims, 9 Drawing Sheets

(51) Int. Cl.
  *G06N 7/00* (2023.01)
  *A61F 2/72* (2006.01)
(52) U.S. Cl.
  CPC . *A61B 2562/0252* (2013.01); *A61B 2562/046* (2013.01)
(58) Field of Classification Search
  CPC ... A61B 5/6824; A61B 5/7246; A61B 5/7282; A61B 5/6828; G06K 9/6256; G06N 7/00; G06F 3/015; A61F 2/7812; A61F 2/72; A61F 2002/6872; A61F 2002/701; A61F 2002/704; A61F 2/68; A61F 2/70; G16H 40/63
  See application file for complete search history.

(56) References Cited

U.S. PATENT DOCUMENTS

| | | | |
|---|---|---|---|
| 7,826,894 | B2 | 11/2010 | Musallam et al. |
| 8,437,844 | B2 | 5/2013 | Momen et al. |
| 8,504,146 | B2 | 8/2013 | Joshi et al. |
| 8,512,415 | B2 | 8/2013 | Herr et al. |
| 8,588,977 | B2 | 11/2013 | Engeberg et al. |
| 9,155,487 | B2 | 10/2015 | Linderman et al. |
| 2012/0010749 | A1 | 1/2012 | Van Der Merwe et al. |
| 2012/0310370 | A1 | 12/2012 | Huang et al. |
| 2014/0031952 | A1 | 1/2014 | Harshbarger et al. |
| 2014/0058528 | A1 | 2/2014 | Contreras-Vidal et al. |
| 2014/0364703 | A1 | 12/2014 | Kim et al. |
| 2014/0371871 | A1 | 12/2014 | Farina et al. |
| 2016/0113587 | A1 | 4/2016 | Kothe et al. |

OTHER PUBLICATIONS

Widjaja, Ferdinan, et al. "Kalman filtering of accelerometer and electromyography (EMG) data in pathological tremor sensing system." 2008 IEEE International Conference on Robotics and Automation. IEEE, 2008. (Year: 2008).*
Tian, Pan, et al. "Application of multi-output support vector regression on EMGs to decode hand continuous movement trajectory." Bio-Medical Materials and Engineering 26.s1 (2015): S575-S582. (Year: 2015).*
Di Pascoli, Stefano, et al. "Design and implementation of a wireless in-ovo EEG/EMG recorder." IEEE transactions on biomedical circuits and systems 7.6 (2013): 832-840. (Year: 2013).*
Chen et al.; "Multiple Hand Gesture Recognition Based on Surface EMG Signal." 2007 1st International Conference on Bioinformatics and Biomedical Engineering; IEEE; 2007; pp. 506-509.
Cipriani et al.; "On The Shared Control of an EMG-Controlled Prosthetic Hand: Analysis of User-Prosthesis Interaction." IEEE Transactions on Robotics; IEEE; Feb. 25, 2008; vol. 24, Issue 1; pp. 170-184.
Cipriani et al.; "Dexterous Control of a Prosthetic Hand Using Fine-Wire Intramuscular Electrodes in Targeted Extrinsic Muscles." Transactions on Neural Systems and Rehabilitation Engineering; IEEE; Jan. 21, 2014; vol. 22, Issue 4; pp. 828-836.
Davis et al.; "Restoring Motor Control and Sensory Feedback in People with upper Extremity Amputations Using Arrays of 96 Microelectrodes Implanted in the Median and Ulnar Nerves." Journal of Neural Engineering; IOP Publishing; vol. 13; Mar. 22, 2016; pp. 1-15.
Harada et al.; "Robot Finger Design for Myoelectric Prosthetic Hand and Recognition of Finger Motions via Surface EMG." 2010 IEEE International Conference on Automoation and Logistics; IEEE; Aug. 2010; pp. 273-278.
Huang et al.; "Development of a Myoelectric Discrimination System for a Multi-Degree Prosthetic hand." Proceedings 1999 IEEE International Conference on Robotics and Automation; IEEE; May 1999; pp. 2392-2397.
Muceli et al.; "Simultaneous and Proportional Estimation of Hand Kinematics From EMG During Mirrored Movements at Multiple Degrees-of-Freedom." IEEE Transactions on Neural Systems and Rehabilitation Engineering; IEEE; Dec. 13, 2011; vol. 20, Issue 3; pp. 371-378.
PCT Application No. PCT/US2017/044947, Filing Date Aug. 1, 2017; Suzanne Wendelken International Search Report, dated Oct. 6, 2017; 11 Pages.
Raspopovic et al.; "Restoring Natural Sensory Feedback in Real-Time Bidirectional Hand Prostheses." Science Translational Medicine; vol. 6, Issue 222; Feb. 5, 2014; pp. 222ra19.
Sonone et al.; "Real Time Control of Robotic Arm Using Electromyogram (EMG) Signals." International Journal of Science and Research (IJSR); 2016; vol. 5, Issue 1; 21 Pages.
Tenore et al.; "Towards the Control of Individual Fingers of a Prosthetic Hand Using Surface EMG Signals." 2007 29th Annual International Conference of the IEEE Engineering in Medicine and Biology Society; IEEE; Aug. 2007; pp. 6145-6148.
Zhou et al.; "Decoding a New Neural-Machine Interface for Control of Artificial Limbs." Journal of Neurophysiology; American Physiological Society; Aug. 29, 2007; vol. 98; pp. 2974-2982.
Butler et al.; "Electromyographic assessment of trunk muscle activation amplitudes during a simulated lifting task using pattern recognition techniques." Journal of Electromyography and Kinesiology; Elsevier; Dec. 1, 2009; vol. 19, No. 6; pp. e505-e512.
Wang et al.; "A portable artificial robotic hand controlled by EMG signal using ANN classifier." 2015 IEEE International Conference on Information and Automation, IEEE; Aug. 8, 2015; pp. 2709-2714.
Gajendran et al.; "Crosspoint switching of EMG signals to increase number of channels for pattern recognition myoelectric control." 2013 6th International IEEE/EMBS Conference on Neural Engineering (NER), IEEE, Nov. 6, 2013; pp. 259-262.
Geng et al.; "A novel channel selection method for multiple motion classification using high-density electromyography." Biomedical Engineering Online, Biomed Central LTD. London, GB, Jul. 25, 2014; vol. 13, No. 1; p. 102.
Hahne et al.; "Linear and Nonlinear Regression Techniques for Simultaneous and Proportional Myoelectric Control." IEEE Transactions on Neural Systems and Rehabilitationengineering, IEE Service Center, New York, NY, US, Mar. 1, 2014; vol. 22, No. 2; pp. 269-279.
Noda et al.; "An electromyogram based force control coordinated in assistive interaction." 2013 IEEE International Conference on Robotics and Automation (ICRA); May 6-10, 2013; Karlsruhe, Germany, IEEE, US, May 6, 2013; pp. 2657-2662.
Osu et al.; "Feedforward impedance control efficiently reduce motor variability." Neuroscience Research; Elsevier; Sep. 1, 2009; vol. 65, Issue 1; 19 Pages.

(56) References Cited

OTHER PUBLICATIONS

Zhang et al.; "Comparison of online adaptive learning algorithms for myoelectric hand control." 2016 $9^{th}$ International conference on human system interactions (HSI), IEEE, Jul. 6, 2016; pp. 69-75.

* cited by examiner

SIGNAL PROCESSING FOR DECODING INTENDED MOVEMENTS FROM ELECTROMYOGRAPHIC SIGNALS

RELATED APPLICATION(S)

This application claims the benefit of U.S. Provisional Application No. 62/512,576, filed May 30, 2017 and U.S. Provisional Application No. 62/369,496, filed Aug. 1, 2016 which are each incorporated herein by reference.

GOVERNMENT INTEREST

This invention was made with government support under Grant No. N66001-12-C-4042 and N66001-15-C-4017 awarded by U.S. Department of Defense. The government has certain rights in the invention.

BACKGROUND

Amputation of all or part of a limb, whether by trauma or by disease, is a particularly debilitating condition and greatly impacts the quality of life of the amputee. Although there are a variety of prosthetics that restore basic function, current prosthetic options lack the dexterity of control needed to replace full function. Commercially available myoelectric prosthetic arms utilize a simple, low degree of freedom (DOF) decode method that uses a limited number of precisely placed surface EMG (sEMG) electrodes whose signals are directly assigned to individual DOFs. As a result, the user can only control a few (e.g., 2-3) DOFs of control of the prosthetic. Additionally, graded movements are difficult for the user, and initiation of movement may require a high level of muscle contraction, which can be both frustrating and fatiguing for the user.

SUMMARY

A technology is described for signal processing that decodes intended limb movements from surface or intramuscular electromyographic signals. In one example, there is provided a system for determining an intended movement from neuromuscular signals, comprising:
  an electrode array;
  at least one processor;
  a memory device including instructions that, when executed by the at least one processor, cause the system to:
    receive electromyography (EMG) data via single-ended channels of the electrode array, wherein the EMG data is associated with a training movement performed by a user in response to receiving a training movement cue;
    determine differential channel pairs for the single-ended channels of the electrode array associated with the EMG data;
    extract feature data from the EMG data of the differential channel pairs;
    align the feature data to movement cue data of the training movement cue;
    select a feature data set from the feature data as training input to a decode model configured to correlate the feature data set to an intended movement; and
    configure the decode model using the feature data set.

In one example of the system for determining an intended movement from neuromuscular signals, the electrode array comprises a surface electrode array.

In one example of the system for determining an intended movement from neuromuscular signals, the memory device includes instructions that, when executed by the processor, cause the system to further extract the feature data from the EMG data of the single-ended channels of the electrode array.

In one example of the system for determining an intended movement from neuromuscular signals, the feature data is aligned to the training movement cue using at least one of: a global shift correlation technique, a global shift recursive regression technique, a trial by trial correlation technique, or a trial by trial recursive regression technique.

In one example of the system for determining an intended movement from neuromuscular signals, the feature data set is selected from the feature data of differential channel pairs using a Gram-Schmidt or recursive regression technique.

In one example of the system for determining an intended movement from neuromuscular signals, the feature data set is selected from the feature data of differential channel pairs having a higher correlation with training movement data as compared to the feature data of other differential channel pairs.

In one example of the system for determining an intended movement from neuromuscular signals, the feature data set is manually selected.

In one example of the system for determining an intended movement from neuromuscular signals, the memory device includes instructions that, when executed by the processor, cause the system to further modify decode output data set using a gain parameter and a threshold parameter to control sensitivity and stability of decode output provided by the decode model.

In one example of the system for determining an intended movement from neuromuscular signals, the memory device includes instructions that, when executed by the processor, cause the system to further update decode model coefficients using a new feature data set obtained via new training movement cue data.

In one example of the system for determining an intended movement from neuromuscular signals, the decode model comprises any one or more of: a Kalman filter model, a direct weighted ridge regression Kalman filter model, a Recalibrated Feedback Intention-Trained (Re-FIT) Kalman filter model, a linear regression model, a support vector regression model, a non-linear support vector regression model, or a neural network model.

In one example, there is provided a computer implemented method for determining an intended movement from neuromuscular signals, comprising:
  receiving electromyography (EMG) data corresponding to single-ended channels of an electrode array, wherein EMG signals are detected by electrodes comprising the single-ended channels of the electrode array and the EMG signals are converted to the EMG data;
  determining differential channel pairs for the single-ended channels of the electrode array;
  extracting feature data from the EMG data of the differential channel pairs;
  selecting a feature data set from the feature data of the differential channel pairs;
  inputting the feature data set to a decode model configured to correlate the feature data set to an intended movement;
  receiving decode output from the decode model indicating the intended movement;
  and providing the decode output to a device.

In one example of the computer implemented method for determining an intended movement from neuromuscular signals, the feature data set is selected from the feature data of the differential channel pairs further comprises calculating EMG amplitudes for the differential channel pairs using the EMG data and selecting the feature data set based in part on the EMG amplitudes.

In one example of the computer implemented method for determining an intended movement from neuromuscular signals, where inputting the feature data set to the decode model further comprises inputting regression coefficient parameters and degrees of freedom (DOF) parameters.

In one example of the computer implemented method for determining an intended movement from neuromuscular signals, the coefficient parameters are updated with each cycle of input to the decode model.

In one example of the computer implemented method for determining an intended movement from neuromuscular signals, DOF gains parameters and DOF threshold parameters are received from a user, and the DOF gains parameters and DOF threshold parameters are applied to the decode output.

In one example of the computer implemented method for determining an intended movement from neuromuscular signals, a movement mode parameter is received from a user, where the movement mode parameter specifies: a position control mode where decode output represents position and each DOF returns to a neutral baseline position during non-activity, a latching mode where decode output represents velocity that is integrated to give position and each DOF maintains a fixed position during non-activity, and a leaky mode comprising a combination of the position control mode and the latching mode where decode output represents velocity that is integrated to give position but each DOF returns to a neutral baseline position during non-activity. Further, different movement modes can be assigned to each DOF individually. For example, latching mode can be assigned to wrist movements and position mode to the individual fingers. Such an approach allows the wrist to maintain its position while the fingers perform a dexterous task.

In one example of the computer implemented method for determining an intended movement from neuromuscular signals, where providing the decode output to the device further comprises providing the decode output to a prosthesis device.

In one example of the computer implemented method for determining an intended movement from neuromuscular signals, where providing the decode output to the device further comprises providing the decode output to a control device.

In one example, there is provided a non-transitory machine readable storage medium having instructions embodied thereon, the instructions when executed by a processor:
  receive electromyography (EMG) data corresponding to single-ended channels of an electrode array;
  determine differential channel pairs for the single-ended channels of the electrode array;
  calculate EMG amplitudes for the differential channel pairs and the single-ended channels of the electrode array using the EMG data;
  select a feature data set from the EMG data of the differential channel pairs and the single-ended channels of the electrode array based in part on the EMG amplitudes;
  input the feature data set to a decode model configured to estimate an intended movement based on the feature data set;
  receive decode output from the decode model indicating the intended movement; and
  provide the decode output to a device.

In one example of the non-transitory machine readable storage medium, the electrode array comprises a surface electrode array.

In one example of the non-transitory machine readable storage medium, the electrode array comprises an implanted electrode array.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

Figure 1:
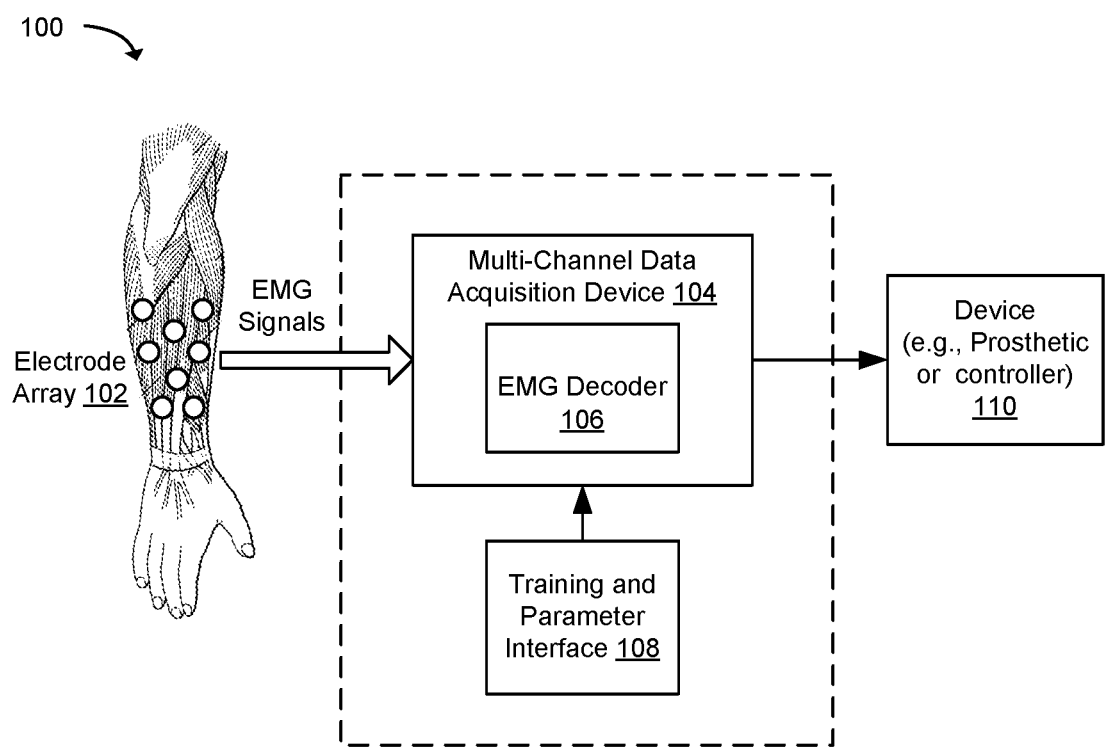
FIG. 1 is a diagram illustrating an example system used to receive EMG signals from a user and decode the EMG signals to determine the user's intended movement.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "an electrode" includes reference to one or more of such devices and reference to "subjecting" refers to one or more such steps.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, and combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

The technology described herein relates to determining an intended movement encoded in neuromuscular signals received from an array of surface or intramuscular electrodes attached to a user. In one aspect, the technology can be used by amputees to control a robotic prosthetic (e.g., a hand prosthetic or foot prosthetic) by way of neuromuscular signals detected using an electrode array attached to the amputees residual limb. As one example, a robotic hand prosthetic fitted for an amputee can be controlled by the amputee by detecting EMG (electromyography) signals using an electrode array attached to the amputees residual limb and decoding the EMG signals using an estimation technique and/or predictive technique to determine multiple degrees of freedom (DOF) control that can be used to control the robotic hand prosthetic.

In another aspect, the technology may allow a user to control a device, such as, but not limited to, a remote robotic arm and hand used for surgical, hazardous environment, space, and underwater applications, joystick, game controller, or computer input device. The device can be controlled using an electrode array to detect neuromuscular signals of a user, who may or may not be an amputee. As one example, a user can wear a cuff or sleeve that contains an electrode array used to detect EMG signals that can be decoded using an estimation technique and/or predictive technique to determine multiple degrees of freedom (DOF) control used to control the input functions of a video game controller.

Furthermore, this system can be used for rehabilitation, prosthetic control, or the like for any muscle group. Non-limiting examples can include back, legs, torso, feet, and the like. In another example, the system can be used with individuals having congenital defects of missing limbs, amputees, spinal cord injury, and the like. For example, this system can be used to restore movement using a prosthetic hand (or other controllable devices) after spinal cord injury in cases where control of the biceps is spared but control of more distal hand muscles is lost. In yet another aspect, the muscle control signals from one muscle group can be applied to movement of a distinct prosthetic. For example, bicep muscles can in some cases be trained to control prosthetic hand movement.

A filter based signal processing method can be used for decoding intended movements from surface or intramuscular electrodes. Feature data derived from EMG signals of any number of electrodes can be input to the signal processing method and output can be used to control an advanced virtual or robotic prosthetic arm capable of individual digit, wrist, elbow, and shoulder control (elbow, and shoulder control for transhumoral and above amputees), or to control various types of control devices, such as computing input devices and game controllers. Alternatively, the technology can be used to bridge paralyzed or blocked nerve sections to restore movement in conjunction with stimulation electrodes.

In one example, the signal processing method uses a predictive model, such as a Kalman filter, to predict intended movements based in part on EMG signals detected by surface or intramuscular electrodes of a user. Output of the signal processing method can include digital signal controls to individual actuators controlling components of a device, such as a prosthetic device. Illustratively, the signal processing method can provide a user with real time, proportional, intuitive control of individual components of a prosthetic device, without the need for manual switching between different movement modes or recalibration by a prosthetist, as is involved by most current commercially available EMG prosthetic arms. The predictive model used by the signal processing method can be trained using a short calibration sequence where a user follows a sequence of movements of a virtual or actual prosthetic limb. Output of the training can be tuned by the user by means of adjusting threshold and gain settings as needed for each direction of each degree of freedom.

In contrast to past technologies, the present technology provides real-time, intuitive proportional control of individual degrees of freedom of a device, allowing for an infinite number of, for example, grip possibilities and arm positions of a prosthetic arm device. Additionally, the signal processing method can take inputs from any number or type of EMG electrodes. EMG features can be calculated from individual electrodes and/or differential channel pairs, increasing the number of unique signal patterns that can be used in by the signal processing method. The greater number of unique signals used may result in finer, more complex control of a device, for example, providing dexterous, intuitive control of a prosthetic arm and/or hand by upper limb amputees.

To further describe the present technology, examples are now provided with reference to the figures. FIG. 1 is a diagram illustrating a high level example of a system 100 used to receive EMG signals from a user and decode the EMG signals to determine the user's intended movement, allowing the user to control a device 110. A user may be an amputee or a non-amputee. As illustrated, a user can be fitted with an electrode array 102. The electrode array 102 may comprise surface electrodes that are placed in contact with a user's skin (e.g., using an electrode cuff or sleeve illustrated in FIGS. 2a-b and FIG. 3) or implanted electromyographic electrodes and/or an implanted microelectrode array implanted into the muscles and/or nerves of a user's limb.

In the case that an implanted electrode array is used, a microelectrode array, such as a Utah Slanted Electrode Array (USEA), designed to interface with peripheral nerves can be implanted into a user's nerve. The microelectrode array may contain electrode tines ranging in length from 0.5 to 1.5 mm, for example, which can be designed to penetrate into increasing depths of a nerve, thereby accessing multiple fascicles of the nerve. Notably, signals from implanted electrodes can be processed in substantially the same manner as signals from surface electrodes. In many cases, the only difference would be in the electrode hardware rather than in the processing system.

The electrode array 102 detects EMG signal and transmits the EMG signals to a multi-channel data acquisition device 104. The multi-channel data acquisition device 104 can comprise a neural interface processor configured to process EMG signals received from the electrode array 102. Illustratively, the multi-channel data acquisition device 104 may include a high-pass filter (e.g., 0.3 Hz) and a low-pass (LP) filter (e.g., 7.5 kHz), and may sample between 500 Hz and 1 kHz, for example. The multi-channel data acquisition device 104 may amplify and digitize EMG signals (e.g., 16 bit, ~0.2 uV/bit over a range of +/−6.5 mV, with digitization >=8 bits). Further, the multi-channel data acquisition device 104 may include a band pass filter (e.g., 15-375 Hz, with a rate of +/−50% of each range), and a notch filter (e.g., 60/120/180 Hz United States or 50/100/150 Hz Europe) used to reduce 60 Hz power noise. The multi-channel data acquisition device 104 outputs n single-ended channels of filtered EMG data, where n corresponds to a number of electrodes included in an electrode array 102. For example, an electrode array 102 having 32 electrodes provides 32 single-ended channels of EMG signals to the multi-channel data acquisition device 104, which processes the EMG signals and outputs 32 single-ended channels of filtered EMG data.

An EMG decoder 106 can be configured to process the EMG data output by the multi-channel data acquisition device 104 and provide decode output (e.g., movement data) to a device 110, such as a prosthetic device (e.g., a robotic hand or foot) or a type of control device (e.g., computer input device or game controller). Processing the EMG data may include determining a number of input channels of EMG data, as explained below, and selecting EMG features from the input channels for input into a decode model. The EMG decoder 106 may include a decode model configured to provide decode output representing a user's intended movement. The input channels may be determined by identifying the number of single-ended channels included in the electrode array 102 and computing possible differential channel pairs for the single-ended channels. As a more specific example, the electrode array 102 includes n single-ended channels that transmit EMG signals to the multi-channel data acquisition device 104, which processes the EMG signals and provides n single-ended channels of EMG data to the EMG decoder 106. In receiving the n single-ended channels of EMG data, the EMG decoder 106 then computes possible differential channel pairs for the n single-ended channels of EMG data (e.g., where n=32 channels of EMG data, the EMG decoder 106 computes 992 possible differential channel pairs).

Having computed the differential channel pairs, in one example, the EMG decoder 106 may compute EMG amplitudes for each input channel (e.g., single-ended channels and differential channel pairs) of EMG data. The EMG amplitudes provide unique signal patterns associated with the input channels. In another example, EMG amplitudes can be computed for just the input channels comprising the single-ended channels, or EMG amplitudes can be computed for just the input channels comprising the differential channel pairs.

The EMG decoder 106 may be configured to select EMG features from the input channels and input the EMG features (EMG feature data) to the decode model. EMG feature data may comprise EMG amplitude patterns selected from the input channels. Different methods can be used to select the EMG features. For example, EMG features can be selected using a correlation method, using a regression method (e.g., Gram-Schmidt regression), using a combination of a correlation method and a regression method, or using a manual selection method.

The decode model correlates the EMG feature data set to an intended movement and provides decode output data for the intended movement, which can be used to control a device 110. In one example, the decode model may comprise a predictive model, such as a Kalman filter, that combines EMG feature data to predict an intended movement of a user. The decode model can be trained using training data as described in greater detail later in association with FIG. 6.

As illustrated, a user can be provided with a training and parameter interface 108 that allows the user to set EMG decoder 106 parameters and train the decode model included in the EMG decoder 106. For example, a user can set signal gains and thresholds for the EMG decoder 106 that are applied to decode output. The signal gains and thresholds may provide a trade-off between sensitivity and specificity of control of a device 110. For example, higher gain and threshold settings may result in less effort to control a device 110, but may also result in increased cross-talk between input channels. Whereas, lower gain and threshold settings may result in increased effort to control the device 110 and decreased cross-talk between input channels. A user can train the decode model included in the EMG decoder 106 using the training and parameter interface 108. For example, the training and parameter interface 108 can be configured to provide visual and/or audio training movement cues to a user. Training data can be collected from the electrode array 102 while the user follows the training movement cues and the training data can be used to train the decode model.

In one example, the training and parameter interface 108 can be integrated into a device 110, such as a prosthetic, allowing a user to train and tune the EMG decoder 106 without the need of additional equipment. In another example, the training and parameter interface 108 may be provided to a user via a client device, such as mobile device, computing device, gaming console, a remote control, etc. The client device may be in communication with the EMG decoder 106 via a wired or wireless interface.

Figure 2A:
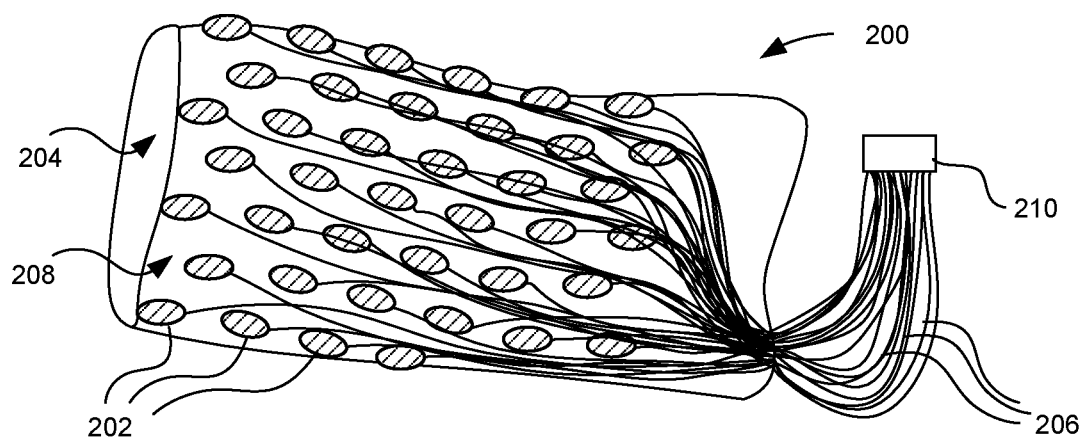
FIGS. 2a-b illustrate an example EMG sleeve that includes an electrode array used to detect neuromuscular signals.
Figure 2B:
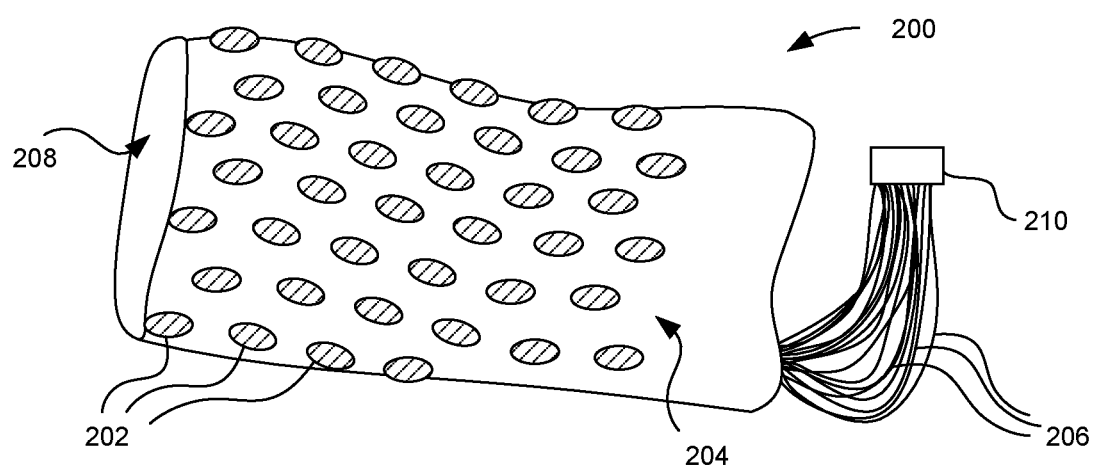

FIGS. 2a-2b illustrate an example EMG sleeve 200 for use with a limb such as a forearm or thigh, that includes an electrode array used to detect neuromuscular signals. The electrode array can include a plurality of individual electrodes 202 distributed along at least an inner surface 204 of the sleeve. Typically each electrode can have a signal line 206. FIG. 2a illustrates an outer surface 208 of the EMG sleeve 200 where electrodes need not necessarily be exposed. FIG. 2b illustrates the EMG sleeve 200 of FIG. 2a turned inside-out showing electrodes exposed along with signal lines for each electrode. If insulated, signal lines can be directed along either outside or inside surfaces of the EMG sleeve. The signal lines 206 can be electrically connected to a plug or connector 210. The connector 210 can be any suitable electrical connector which allows signals to be electrically communicated to a corresponding processor for decoding. As illustrated, the EMG sleeve may comprise a material, such as neoprene, studded with electrodes. The number of electrodes may vary depending upon the size of the EMG sleeve. For example, in the case that the EMG sleeve is fitted for an amputee, the number of electrodes may depend upon an amount of surface area that is available on the amputee's residual limb. The electrodes can include a reference electrode and a ground electrode. The ground electrode can be placed in a location on the EMG sleeve that places the ground electrode in proximity to a ground location of a user's limb. For example, in the case that the EMG sleeve is fitted for a user's arm, the ground electrode can be placed on the EMG sleeve such that the ground electrode is located in proximity to the ulna bone near the user's elbow. As will be appreciated, the EMG sleeve can be fitted for both amputee's and non-amputees and can be configured for use with any human extremity.

Figure 3:
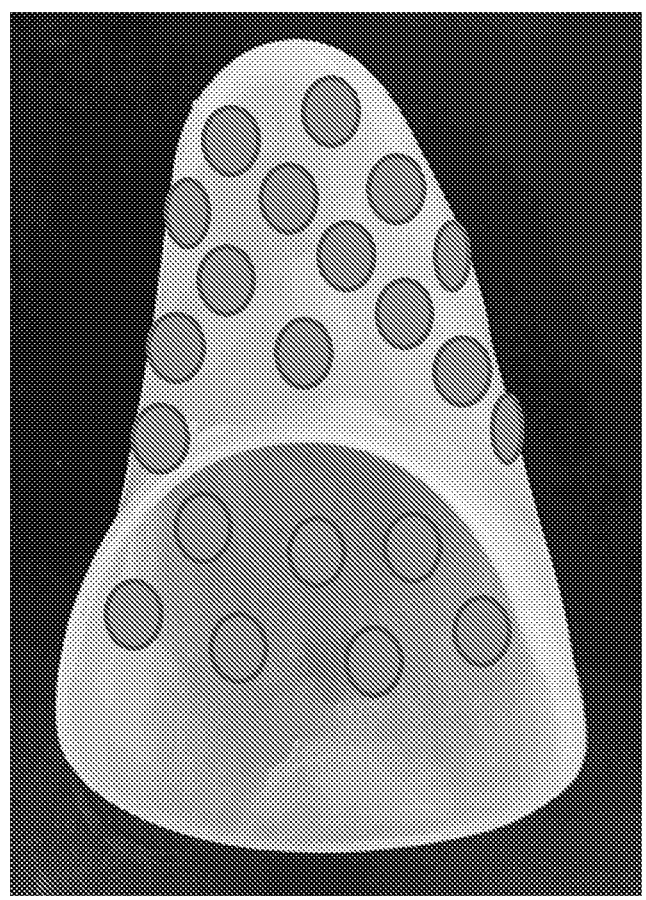
FIG. 3 illustrates an example molded EMG liner that includes an electrode array used to detect neuromuscular signals.

FIG. 3 illustrates an example molded EMG liner that includes an electrode array used to detect neuromuscular signals similar to the EMG sleeve illustrated in FIG. 2a-b. The EMG liner may comprise a moldable material, such as plastic, polyurethane rubber, silicone, or the like. Like the EMG sleeve described above, the EMG liner can include a number of electrodes, which can vary depending upon the available surface area of the EMG liner. In one example, the electrodes can be embedded into the moldable material of the EMG liner, such that a surface of the electrodes is in contact with the skin of the user's limb. In another example, the electrodes can be attached to the surface of the EMG liner in a configuration that places a surface of the electrodes in contact with the skin of the user's limb. The EMG liner can include a reference electrode and a ground electrode as described above. The EMG liner can be configured for use with any incomplete human extremity such as, but not limited to, upper limb (e.g. bicep, forearm, wrist), lower limb (e,g, thigh, calf, foot). More specifically, the an interior surface of the liner can engage with the skin while a prosthetic device (e.g. hand, wrist assembly) can be mounted on a distal outer surface of the molded EMG liner.

Figure 4:
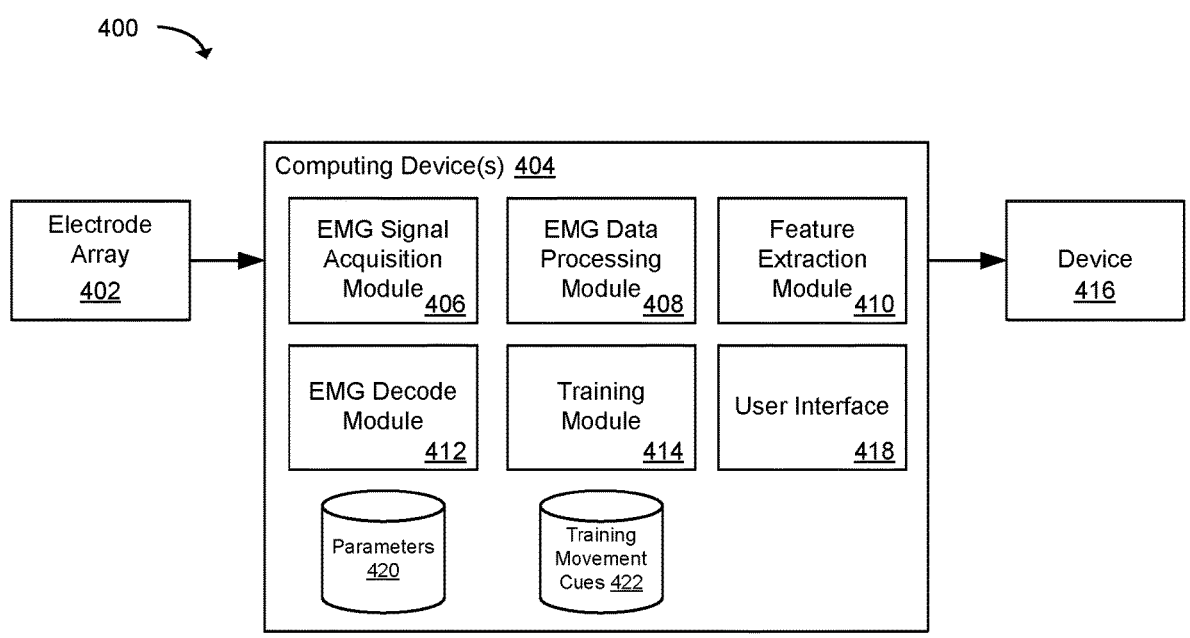
FIG. 4 is a block diagram illustrating components of an example system on which the present technology may be executed.

FIG. 4 is a block diagram illustrating components of an example system 400 on which the present technology may be executed. The system 400 can be used to determine a user's intended movement, allowing the user to control a device 416. As illustrated, the system 400 can include a computing device 404 that is communicatively coupled to an electrode array 402 and a device 416. The electrode array 402 can comprise an array of surface or intramuscular electrodes attached to a user. In one example, intramuscular electrodes can be implanted into an amputee's residual limb. For example, the intramuscular electrodes can include USEAs (Utah Slanted Electrode Arrays) that are implanted into an amputee's residual limb. In another example, surface electrodes can be attached to a user using a EMG sleeve or EMG liner. The device 416 can include any device that can be controlled using intended movement commands converted from EMG signals and provided to the device 416.

The computing device 404 may include various components used to process EMG signals received from the electrode array 402 and provide intended movement commands to the device 416. In the example illustrated, the computing device 404 includes an EMG acquisition module 406, an EMG data processing module 408, a feature extraction module 410, an EMG decode module 412, a training module 414, and a user interface 418.

The EMG signal acquisition module 406 may be configured to receive EMG signals from the electrode array 402 and convert the EMG signals to EMG data used by the other modules included in the computing device 404. For example, the EMG signal acquisition module 406 receives EMG signals from single-ended channels of electrodes included in the electrode array 402. The EMG signal acquisition module 406 may filter, sample, amplify, and digitize the EMG signals using an EMG data collection method. For example, the EMG signal acquisition module 406 may be configured to use the filters, sample rates, amplification parameters, and digitization parameters described earlier in association with FIG. 1. The EMG signal acquisition module 406 outputs EMG data that corresponds to single-ended channels of the electrode array 402 to the EMG data processing module 408.

The EMG data processing module 408 may be configured to process EMG data received from the EMG signal acquisition module 406. In one example, EMG data processing may comprise: computing differential channel pairs using EMG data corresponding to single-ended channels of the electrode array 402, buffering EMG data for the single-ended channels and the differential channel pairs into input channel bins, and computing EMG amplitudes for each of the input channels. The processed EMG data can then be provided to the feature extraction module 410.

The feature extraction module 410 may be configured to extract EMG feature data from the input channels of EMG data and select a signal feature set based in part on the EMG amplitudes of the input channels. Extracting the EMG feature data may comprise extracting EMG feature data from EMG data of the single-ended channels of the electrode array and/or from EMG data of the differential channel pairs. Selecting EMG features may comprise identifying a EMG feature data set using feature optimization to remove redundant, noisy, or non-specific EMG features from the EMG feature data set. In one example, feature optimization can include using a Gram-Schmidt regression technique to create a EMG feature data set. In another example, a correlation method can be used to select EMG features having a having a higher correlation with training movement data as compared to feature data of other differential channel pairs. In yet another example, a EMG feature data set can be manually selected. As will be appreciated, other feature optimization methods can be used to select EMG features for a EMG feature data set. In some examples, the feature extraction module 410 can be configured to condition EMG features by normalizing EMG feature data. Normalization of EMG feature data may boost the power of smaller signals relative to larger signals.

The EMG decode module 412 may be configured to determine an intended movement using a predictive model. The predictive model can include any one or more of: a Kalman filter model, a direct weighted ridge regression Kalman filter model, a Recalibrated Feedback Intention-Trained (Re-FIT) Kalman filter model, a linear regression model, a support vector regression model, a non-linear support vector regression model, or a neural network model. As will be appreciated, other predictive models not specifically mentioned above can also be used to determine an intended movement. The predictive model can be trained using training data collected during a training session that utilizes the training module 414. EMG feature data received from the feature extraction module 410 is input into the predictive model along with regression coefficients. The predictive model uses the EMG feature data and regression coefficients to determine a user's intended movement.

The training module 414 can be configured to train a predictive model used by the EMG decode module 412. In one example, training data can be collected during a training session in which a user is provided with verbal and/or visual training movement cues 422 that instruct the user to perform a movement (e.g., arm, hand, finger(s), leg, foot movement). In the case that the user is an amputee, the user may be instructed to mentally move a phantom limb. EMG feature data collected during a training session is aligned to training movement cues 422. EMG feature data can be aligned to a training movement cue using at least one of: a correlation technique, a global shift technique, a trial by trial technique, a recursive regression technique, or another data alignment technique. A EMG feature data set can be created using the feature extraction module 410 and the EMG feature data set can be input, along with parameters 420, to the predictive model.

The user interface 418 can be configured for I/O (Input/Output). For example, the user interface 418 can be used for input of parameters 420 (e.g., gain parameters and threshold parameters). Also, the user interface 418 can be configured to walk a user through a training session that collects training data used to train a predictive model utilized by the EMG decode module 412.

Figure 5:
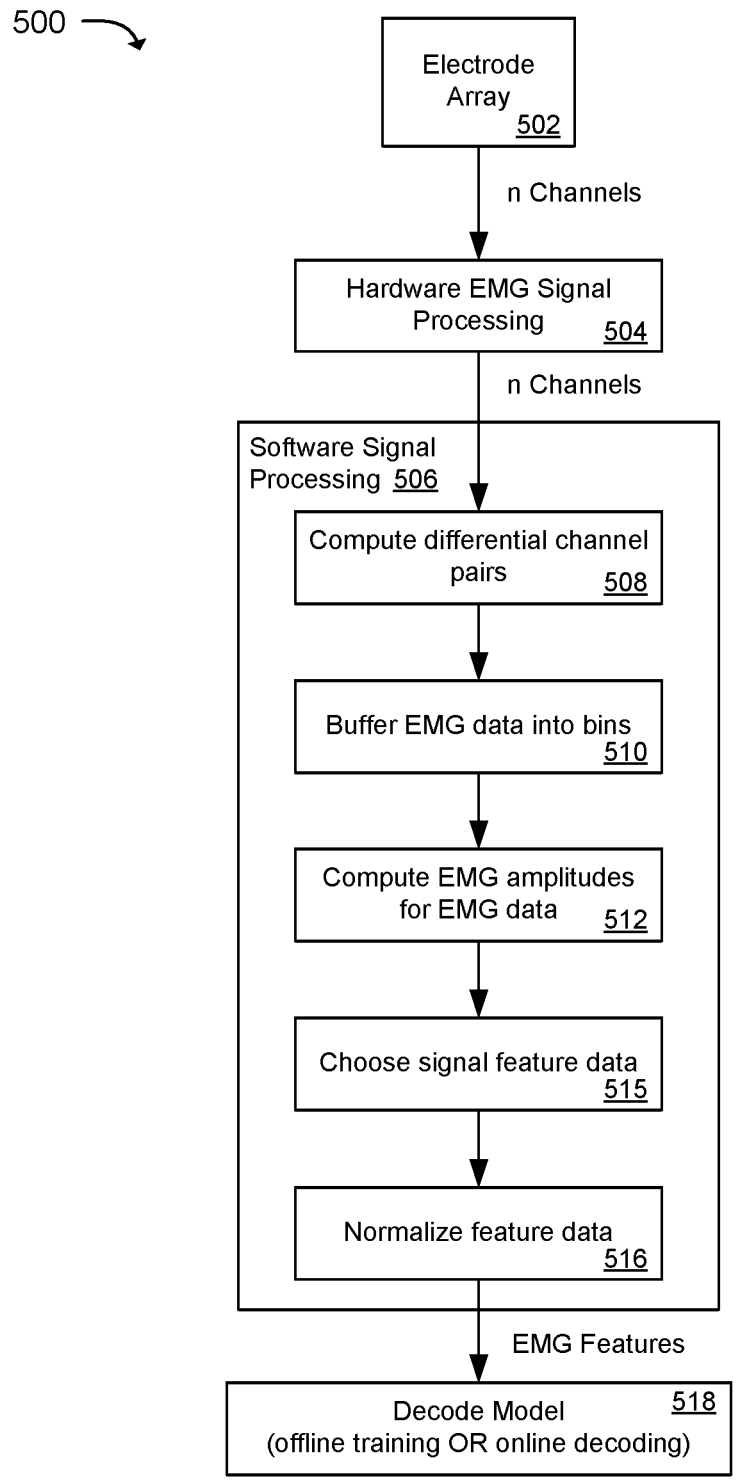
FIG. 5 is a flow diagram illustrating an example method for processing EMG signals.

FIG. 5 is a flow diagram illustrating an example method 500 for processing EMG signals. The method 500 may include receiving EMG signals from an electrode array 502 configured to provide a plurality of single-ended channels of EMG signals. The EMG signals received from the single-ended channels may be processed in hardware 504 using filters and sampling. As a specific example, EMG signals can be processed by applying a high-pass filter 0.3 Hz, a low-pass filter 7.5 kHz, sampling the EMG signals at 1 kHz, amplifying and digitizing the EMG signals at 16 bit, ~0.2 uV/bit over a range of +/−6.5 mV, applying a band pass filter 15-375 Hz, and applying a notch filter 60/120/180 Hz to reduce 60 Hz power noise. Hardware processing of the EMG signals outputs n single-ended channels of filtered EMG data. Continuing the specific example above, hardware processing of 32 single-ended channels of EMG signals outputs 32 single-ended input channels of filtered 1 kHz EMG data.

Having processed the EMG data in hardware, software signal processing 506 can be performed for the n single-ended channels of filtered EMG data. Software signal processing 506 of EMG data can be performed iteratively, so as to detect and identify subsequent user intended movements. For example, a loop time (e.g., 20, 30, or 40 milliseconds) can be used to process EMG data as the EMG data is received from the electrode array 502. As illustrated, software signal processing 506 may comprise computing differential channel pairs 508 for the n single-ended channels of EMG data. In one example, the differential channel pairs can be computed using a matrix multiplication method or by looping through each possible pair individually and calculating the difference. Computing differential channel pairs 508 can provide a better signal to noise ratio (SNR) as compared to using just single-ended channels of EMG data, and can provide a virtual signal source between electrodes in the differential channel pairs. This reduces the need for precise placement of the electrode array on the user's limb and results in a more robust decode.

Next, EMG data for each input channel (single-ended channels and differential channel pairs) can be buffered into bins 510 (also call Kernel width). In one example, the bins can range in size from 60 to 300 milliseconds. EMG amplitudes can then be computed 512 for the buffered EMG data by rectifying and averaging over the bin window. For example, the absolute value of the 1 kHz sampled and band-pass filtered EMG data is computed and then averaged over the bin window. This average value is then updated at a frequency of 30 Hz.

Having computed EMG amplitudes for each of the input channels, EMG feature data can be selected 515 for input to a decode model. In one example, single-ended channels and half the number of possible differential channel pairs are selected for input to the decode model. As a specific example, where the number of single-ended input channels is 32, the possible number of differential channel pairs is 992. Accordingly, half the number of the differential channel pairs are selected (i.e., 496) and combined with the single-ended channels (i.e., 32+496), producing a number of EMG features (i.e., 528) for input to the decode model.

Prior to inputting the selected EMG features to the decode model, the EMG features can be normalized 516. In one example, each EMG feature can be normalized by subtracting all values from the minimum value and then dividing all values by the maximum value. This would result in each EMG feature having a minimum value of 0 and a maximum value of 1. Thereafter, the EMG features are input to the decode model 518 for offline training or online decoding, as described in greater detail below.

Figure 6:
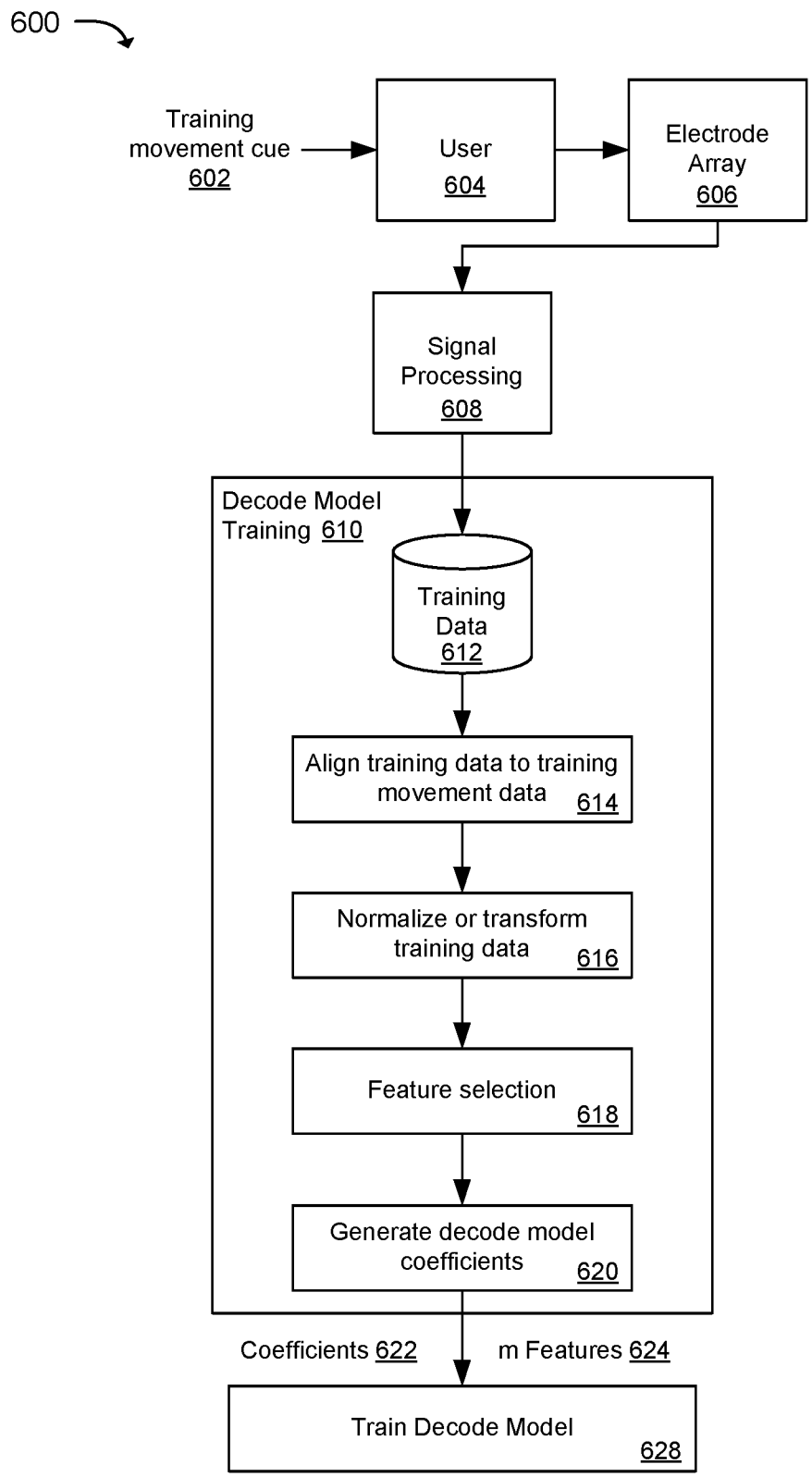
FIG. 6 is a flow diagram that illustrates an example method for training a decode model.

FIG. 6 is a flow diagram that illustrates an example method 600 for training a decode model (offline training). The method 600 may include providing a user 604 with a training movement cue 602 that verbally and/or visually instructs the user 604 to physically/mentally perform a movement. For example, the user may follow training movement cues of a virtual arm/hand or a robotic prosthetic arm/hand, during which training data 612 is collected. The user 604 performs the movement, during which an electrode array 606 detects EMG signals associated with the movement. The EMG signals are processed using the signal processing 608 methods described earlier in reference to FIG. 5 and EMG data can be collected for use in decode model training 610.

Decode model training 610 may comprise aligning training data 612 to training movement data 614 from the training movement cues provided to the user 604. The training data can be aligned to a training movement cue. Illustratively, alignment of the training data to the training movement cue can be performed using a correlation method, a global shift method, a trial by trial method, a recursive regression method, or another data alignment technique.

After aligning the training data, the training data can be normalized or transformed 616. Feature selection 618 can then be performed to select a set of EMG features 624 as described earlier. Coefficient parameters 622 can be generated by inputting selected features and movement cue data to the decode model using one of the described methods (Kalman filter, neural network, etc.) 620 to train 628 the decode model.

After training the decode model, the decode model can be retrained or calibrated periodically. For example, surface electrode movement relative to the skin or muscles after calibration may degrade the performance of the decode model. To mitigate performance issues, a calibration routine can be periodically performed by the user 604. For example, a user 604 can perform a calibration routine that includes performing training movements in response to movement cues and training data 612 can be collected that can be used to retrain the decode model.

Poor training data can also degrade decode model performance. The quality of the decode model may depend on the quality of the training data 612. For example, training data quality may depend on a user 604 performing consistent muscle contractions for a given training movement. If the user is unable to perform consistent training movements, either due to mistakes, improper or variable coordination, resulting from the altered physiology of a residual limb, or attention lapses; the decode model may be poorly trained and the user's ability to accurately control a device may be limited. To mitigate poor training data, an adaptive calibration routine can be applied where the number of training movements may depend on the consistency of collected training data 612 between training movement trials. For instance, the more consistent the user 604 is at performing training movement trials, the fewer trials will be needed to train the decode model.

Figure 7:
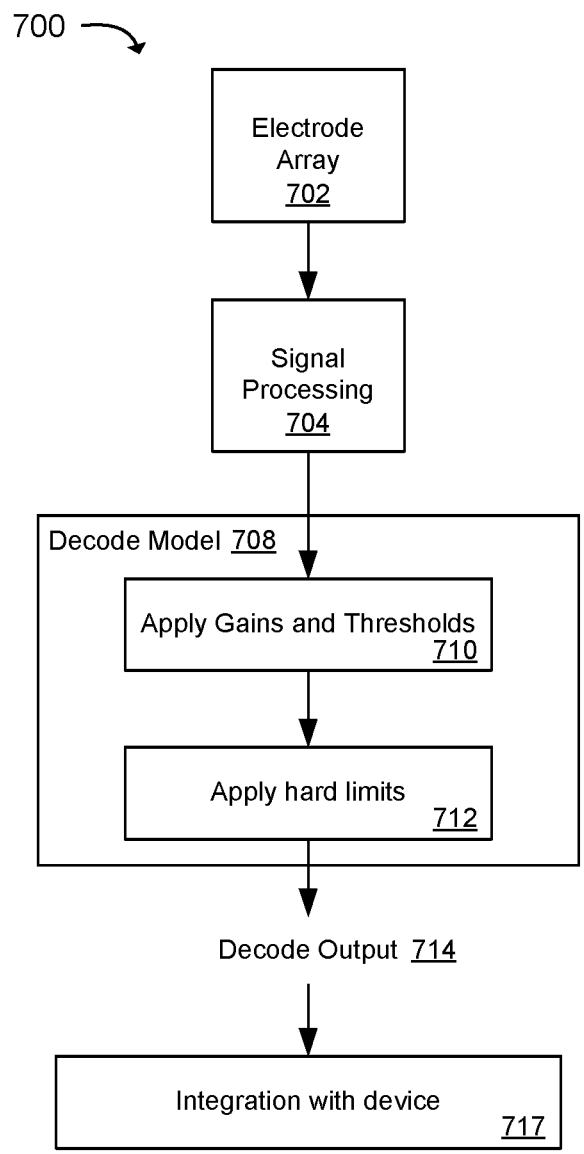
FIG. 7 is a flow diagram illustrating an example method for online decoding of EMG data allowing a device to be controlled in response to a user's intended movement.

FIG. 7 is a flow diagram illustrating an example method 700 for online decoding of EMG data allowing a device to be controlled in response to a user's intended movement. The method 700 may include processing EMG signals received from an electrode array 702 using the signal processing 704 methods described earlier in reference to FIG. 5. An EMG feature data set is provided to a decode model 708, which is trained to correlate the EMG feature data set to an intended movement. The decode model 708 may be configured to apply gains and/or thresholds 710 to decode output. The gains and thresholds may provide a trade-off between sensitivity and specificity of control of a device. For example, higher gain and lower threshold settings may result in less effort to control a device, but may also result in increased cross-talk between decode output channels (DOF). Whereas, lower gain and higher threshold settings may result in increased effort to control the device and decreased cross-talk.

To balance the trade-off between sensitivity and specificity, a dynamic threshold control can be applied. For example, thresholds can be initially set high to reduce cross-talk between the individual DOF. However, when an individual DOF crosses above threshold, the threshold value for that DOF can decrease resulting in less effort to control. During subsequent non-activity when that DOF crosses below the lowered threshold value, threshold will again increase resulting in reduced cross-talk. This idea of a dynamic threshold can be further extended to any model that is applied to the decode output to more closely approximate naturalistic movements and improve dexterity. One example is to apply a model that introduces frictional and elastic components, as well as, interdependencies between DOF to more closely approximate the physics of a physical hand.

Figure 8:
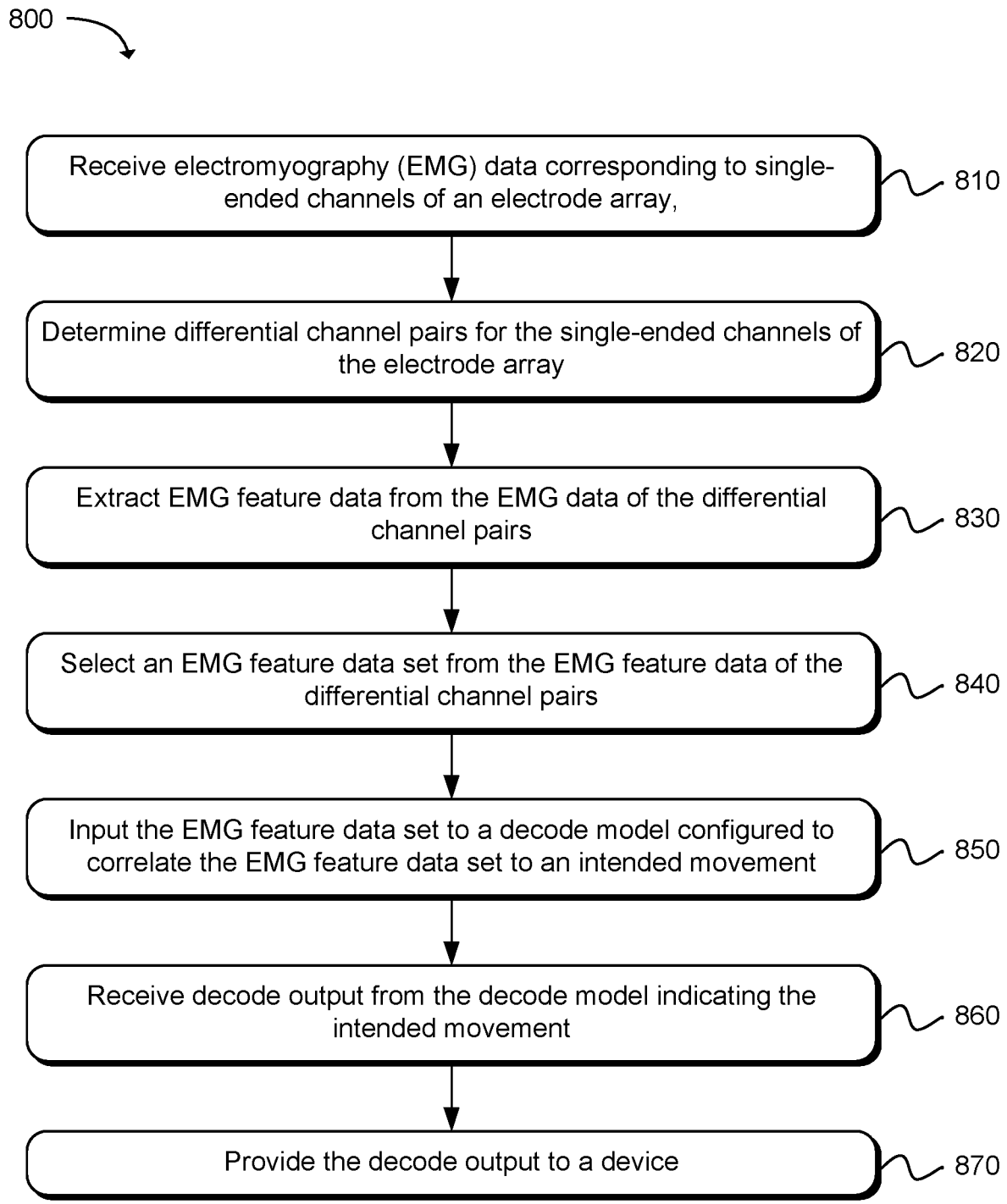
FIG. 8 is a flow diagram that illustrates a method for determining an intended movement from neuromuscular signals.

Also, the decode model 708 may be configured to apply hard limits 712 (e.g., −1:1) to decode output 714. Hard limits can prevent the decode output from reaching unrealistically high values that can result in unwanted pauses and poor performance in device control. Decode output 714 generated by the decode model 708 can be provided to a device as part of integrating the method 700 with the device 717. Illustratively, the decode output 714 can include commands or instructions transmitted to the device that cause the device to perform a movement that corresponds to the intended movement interpreted by the decode model FIG. 8 is a flow diagram that illustrates a method 800 for determining an intended movement from neuromuscular signals. Starting in block 810, the method 800 may include receiving electromyography (EMG) data corresponding to single-ended channels of an electrode array, where EMG signals are detected by electrodes comprising the single-ended channels of the electrode array and the EMG signals are converted to the EMG data.

As in block 820, differential channel pairs can be determined for the single-ended channels of the electrode array. As in block 830, EMG feature data can then be extracted from the EMG data of the differential channel pairs, and as in block 840, an EMG feature data set can be selected from the EMG feature data of the differential channel pairs. As in block 850, the EMG feature data set can be input to a decode model configured to correlate the EMG feature data set to an intended movement. As in block 860, decode output is then received from the decode model, where the decode output indicates the intended movement, and as in block 870, the decode output can be provided to a device.

Figure 9:
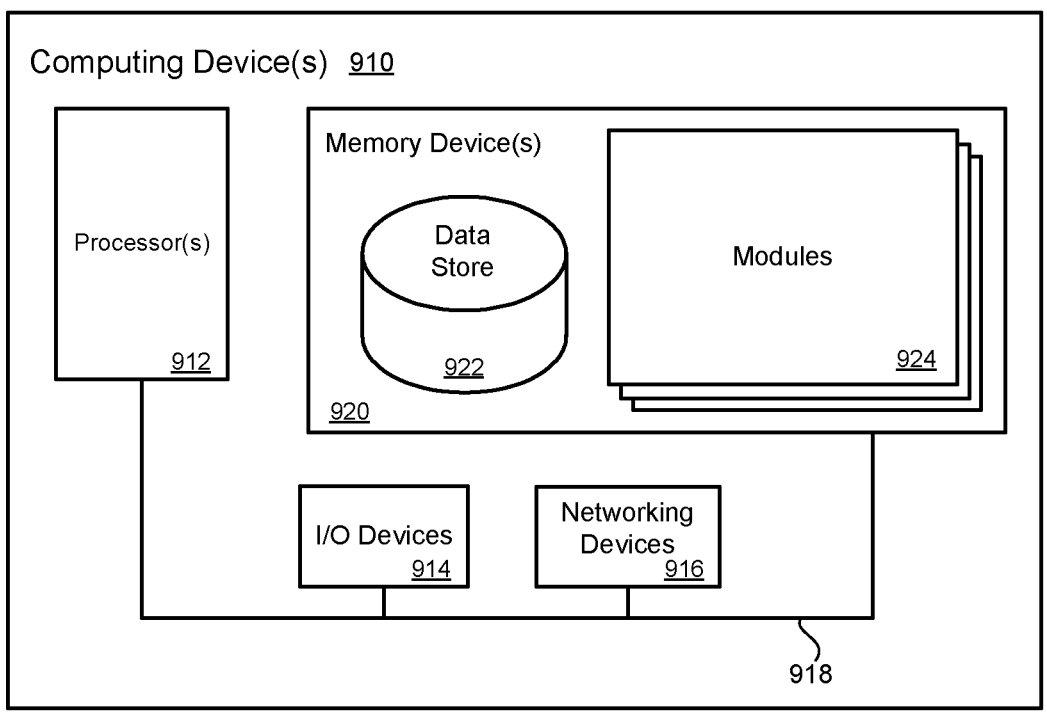
FIG. 9 illustrates a computing device on which modules of this technology may execute.

FIG. 9 illustrates a computing device 910 on which modules of this technology may execute. The computing device 910 may include one or more processors 912 that are in communication with memory devices 920. The computing device 910 may include a local communication interface 918 for the components in the computing device. For example, the local communication interface 918 may be a local data bus and/or any related address or control busses as may be desired.

The memory device 920 may contain modules 924 that are executable by the processor(s) 912 and data for the modules 924. For example, the memory device 920 may include an EMG signal acquisition module, an EMG data processing module, a feature extraction module, an EMG decode module, a training module, and other modules. The modules 924 may execute the functions described earlier. A data store 922 may also be located in the memory device 920 for storing data related to the modules 924 and other applications along with an operating system that is executable by the processor(s) 912.

Other applications may also be stored in the memory device 920 and may be executable by the processor(s) 912. Components or modules discussed in this description that may be implemented in the form of software using high programming level languages that are compiled, interpreted or executed using a hybrid of the methods.

The computing device may also have access to I/O (input/output) devices 914 that are usable by the computing devices. Networking devices 916 and similar communication devices may be included in the computing device. The networking devices 916 may be wired or wireless networking devices that connect to the internet, a LAN, WAN, or other computing network.

The components or modules that are shown as being stored in the memory device 920 may be executed by the processor(s) 912. The term "executable" may mean a program file that is in a form that may be executed by a processor 912. For example, a program in a higher level language may be compiled into machine code in a format that may be loaded into a random access portion of the memory device 920 and executed by the processor 912, or source code may be loaded by another executable program and interpreted to generate instructions in a random access portion of the memory to be executed by a processor. The executable program may be stored in any portion or component of the memory device 920. For example, the memory device 920 may be random access memory (RAM), read only memory (ROM), flash memory, a solid state drive, memory card, a hard drive, optical disk, floppy disk, magnetic tape, or any other memory components.

The processor 912 may represent multiple processors and the memory 920 may represent multiple memory units that operate in parallel to the processing circuits. This may provide parallel processing channels for the processes and data in the system. The local interface 918 may be used as a network to facilitate communication between any of the multiple processors and multiple memories. The local interface 918 may use additional systems designed for coordinating communication such as load balancing, bulk data transfer and similar systems.

While the flowcharts presented for this technology may imply a specific order of execution, the order of execution may differ from what is illustrated. For example, the order of two more blocks may be rearranged relative to the order shown. Further, two or more blocks shown in succession may be executed in parallel or with partial parallelization. In some configurations, one or more blocks shown in the flow chart may be omitted or skipped. Any number of counters, state variables, warning semaphores, or messages might be added to the logical flow for purposes of enhanced utility, accounting, performance, measurement, troubleshooting or for similar reasons.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction, or many instructions and may even be distributed over several different code segments, among different programs and across several memory devices. Similarly, operational data may be identified and illustrated herein within modules and may be embodied in any suitable form and organized within any suitable type of data structure. The operational data may be collected as a single data set, or may be distributed over different locations including over different storage devices. The modules may be passive or active, including agents operable to perform desired functions.

The technology described here may also be stored on a computer readable storage medium that includes volatile and non-volatile, removable and non-removable media implemented with any technology for the storage of information such as computer readable instructions, data structures, program modules, or other data. Computer readable storage media include, but is not limited to, non-transitory media such as RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which may be used to store the desired information and described technology.

The devices described herein may also contain communication connections or networking apparatus and networking connections that allow the devices to communicate with other devices. Communication connections are an example of communication media. Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example and not limitation, communication media includes wired media such as a wired network or direct-wired connection and wireless media such as acoustic, radio frequency, infrared and other wireless media. The term computer readable media as used herein includes communication media.

Reference was made to the examples illustrated in the drawings and specific language was used herein to describe the same. It will nevertheless be understood that no limitation of the scope of the technology is thereby intended. Alterations and further modifications of the features illustrated herein and additional applications of the examples as illustrated herein are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. It will be recognized, however, that the technology may be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements may be devised without departing from the spirit and scope of the described technology.

What is claimed is:

1. A system for determining an intended movement from neuromuscular signals, comprising:
    an electrode array;
    at least one processor;
    a memory device including instructions that, when executed by the at least one processor, cause the system to:
    receive electromyography (EMG) data via single-ended channels of the electrode array,
    wherein the EMG data is associated with a training movement performed by a user in response to receiving a training movement cue;
    determine differential channel pairs for the single-ended channels of the electrode array associated with the EMG data by computing a number of possible different channel pairs for an n number of the single-ended channels using a matrix multiplication method or by looping through possible pairs and calculating a difference;
    extract feature data from the EMG data of the differential channel pairs;
    align the feature data to movement cue data of the training movement cue;
    select a feature data set from the feature data as training input to a decode model configured to correlate the feature data set to an intended movement;
    configure the decode model using the feature data set;
    receive decode output from the decode model indicating the intended movement; and
    provide the decode output to a device.

2. The system as in claim 1, wherein the electrode array comprises a surface electrode array.

3. The system as in claim 1, wherein the memory device includes instructions that, when executed by the processor, cause the system to further extract the feature data from the EMG data of the single-ended channels of the electrode array.

4. The system as in claim 1, wherein the feature data is aligned to the training movement cue using at least one of: a global shift correlation technique, a global shift recursive regression technique, a trial by trial correlation technique, or a trial by trial recursive regression technique.

5. The system as in claim 1, wherein the feature data set is selected from the feature data of differential channel pairs using a Gram-Schmidt or a recursive regression technique.

6. The system as in claim 1, wherein the feature data set is selected from the feature data of differential channel pairs having a higher correlation with training movement data as compared to the feature data of other differential channel pairs.

7. The system as in claim 1, wherein the feature data set is manually selected by a user.

8. The system as in claim 1, wherein the memory device includes instructions that, when executed by the processor, cause the system to further modify decode output data set using a gain parameter and a threshold parameter to control sensitivity and stability of decode output provided by the decode model.

9. The system as in claim 1, wherein the memory device includes instructions that, when executed by the processor, cause the system to further update decode model coefficients using a new feature data set obtained via new training movement cue data.

10. The system as in claim 1, wherein the decode model comprises any one or more of: a Kalman filter model, a direct weighted ridge regression Kalman filter model, a Recalibrated Feedback Intention-Trained (Re-FIT) Kalman filter model, a linear regression model, a support vector regression model, a non-linear support vector regression model, or a neural network model.

11. The system as in claim 1, wherein the EMG data is generated by a user that is an amputee, the device is a robotic prosthetic, and the decode output is employed to control the robotic prosthetic.

12. The system as in claim 1, wherein the device is a remote robotic arm and hand used for surgical, hazardous environment, space, or underwater applications, a joystick, a game controller, or a computer input device.

13. A computer implemented method for determining an intended movement from neuromuscular signals, comprising:
    receiving electromyography (EMG) data corresponding to single-ended channels of an electrode array, wherein EMG signals are detected by electrodes comprising the single-ended channels of the electrode array and the EMG signals are converted to the EMG data;
    determining differential channel pairs for the single-ended channels of the electrode array by computing a number of possible different channel pairs for an n number of the single-ended channels using a matrix multiplication method or by looping through possible pairs and calculating a difference;
    extracting feature data from the EMG data of the differential channel pairs;
    selecting a feature data set from the feature data of the differential channel pairs;
    inputting the feature data set to a decode model configured to correlate the feature data set to an intended movement;
    receiving decode output from the decode model indicating the intended movement; and
    providing the decode output to a device.

14. The method as in claim 13, wherein selecting the feature data set from the feature data of the differential channel pairs further comprises calculating EMG amplitudes for the differential channel pairs using the EMG data and selecting the feature data set based in part on the EMG amplitudes.

15. The method as in claim 13, wherein inputting the feature data set to the decode model further comprises inputting regression coefficient parameters and degrees of freedom (DOF) parameters.

16. The method as in claim 15, further comprising updating the coefficient parameters with each cycle of input to the decode model.

17. The method as in claim 13, further comprising:
    receiving DOF gains parameters and DOF threshold parameters from a user; and
    applying the DOF gains parameters and DOF threshold parameters to the decode output.

18. The method as in claim 13, further comprising receiving a movement mode parameter from a user, wherein the movement mode parameter specifies: a position control mode comprising output for a neutral baseline position associated with non-activity, a latching mode comprising velocity control, and a leaky mode comprising a combination of the position control mode and the latching mode.

19. The method as in claim 13, wherein providing the decode output to the device further comprises providing the decode output to a prosthesis device.

20. The method as in claim 13, wherein providing the decode output to the device further comprises providing the decode output to a control device.

21. A non-transitory machine readable storage medium having instructions embodied thereon, the instructions when executed by a processor:

receive electromyography (EMG) data corresponding to single-ended channels of an electrode array;

determine differential channel pairs for the single-ended channels of the electrode array by computing a number of possible different channel pairs for an n number of the single-ended channels using a matrix multiplication method or by looping through each possible pair and calculating a difference;

calculate EMG amplitudes for the differential channel pairs and the single-ended channels of the electrode array using the EMG data;

select a feature data set from the EMG data of the differential channel pairs and the single-ended channels of the electrode array based in part on the EMG amplitudes;

input the feature data set to a decode model configured to estimate an intended movement based on the feature data set;

receive decode output from the decode model indicating the intended movement; and provide the decode output to a device.

22. The non-transitory machine readable storage medium as in claim 21, wherein the electrode array comprises a surface electrode array or an implanted electrode array.

* * * * *